United States Patent [19]
Krainski, Jr.

[11] 4,314,482
[45] Feb. 9, 1982

[54] ANALOG-DIGITAL CONTROL DEVICE

[75] Inventor: Theodore J. Krainski, Jr., Old Bridge, N.J.

[73] Assignee: Johnson & Johnson, New Brunswick, N.J.

[21] Appl. No.: 149,216

[22] Filed: May 12, 1980

[51] Int. Cl.³ ............................................. G01N 3/00
[52] U.S. Cl. ......................................... 73/805; 73/73
[58] Field of Search ................ 73/790, 805, 806, 811, 73/813, 816, 825, 73

[56] References Cited

U.S. PATENT DOCUMENTS

| | | | |
|---|---|---|---|
| 3,304,768 | 2/1967 | Naumann et al. | 73/816 |
| 3,583,214 | 6/1971 | Kreiskorte et al. | 73/805 |
| 3,803,906 | 4/1974 | Ross | 73/805 |

OTHER PUBLICATIONS

G. B. Kubiceck, "Programming Dynamic Tests", *Instruments & Control Systems*, Mar. 1961, pp. 463-465.

H. T. Strandrud, "Structural Fatigue Testing by Computer Control", Proceedings of the 15th International ISA Aerospace Instrumentation Symposium, May 1969, pp. 249-255.

E. M. Wu, et al. "Computer-Aided Mechanical Testing of Composites", *Materials Research & Standards* vol. 12, No. 2, Feb. 1972, pp. 13-18.

*Primary Examiner*—Charles A. Ruehl
*Attorney, Agent, or Firm*—Donal B. Tobin

[57] ABSTRACT

An analog digital control device having both analog and digital memory with multiple, readily accessible, selectable access ports to allow the control device to be quickly programmed by unskilled personnel and thus render the device particularly useful for the laboratory environment. The device includes a multiplexer switch for receiving both digital and analog input and for generating an output to a comparator to run an external component. An accessing and switching circuit is repeatedly used to access each of the multiple channels of digital memory in sequence.

18 Claims, 8 Drawing Figures

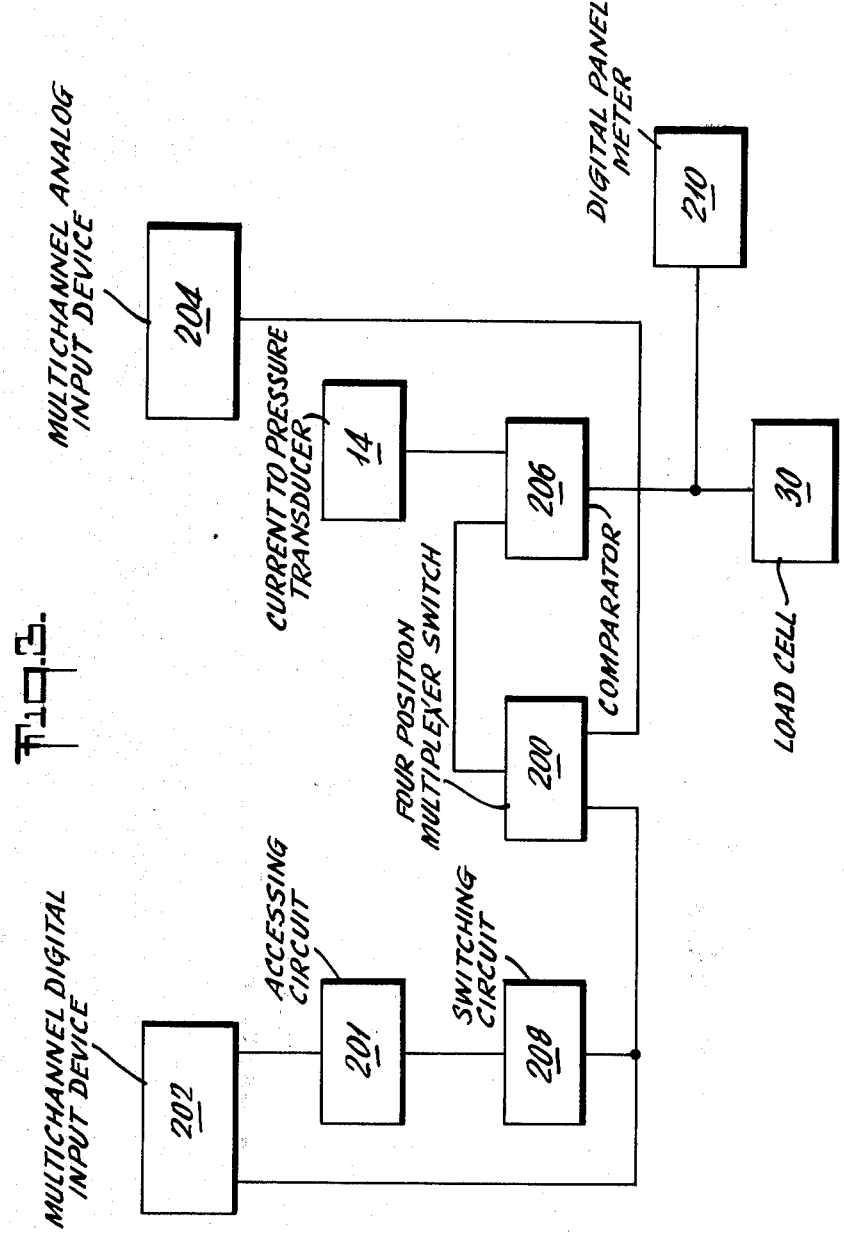

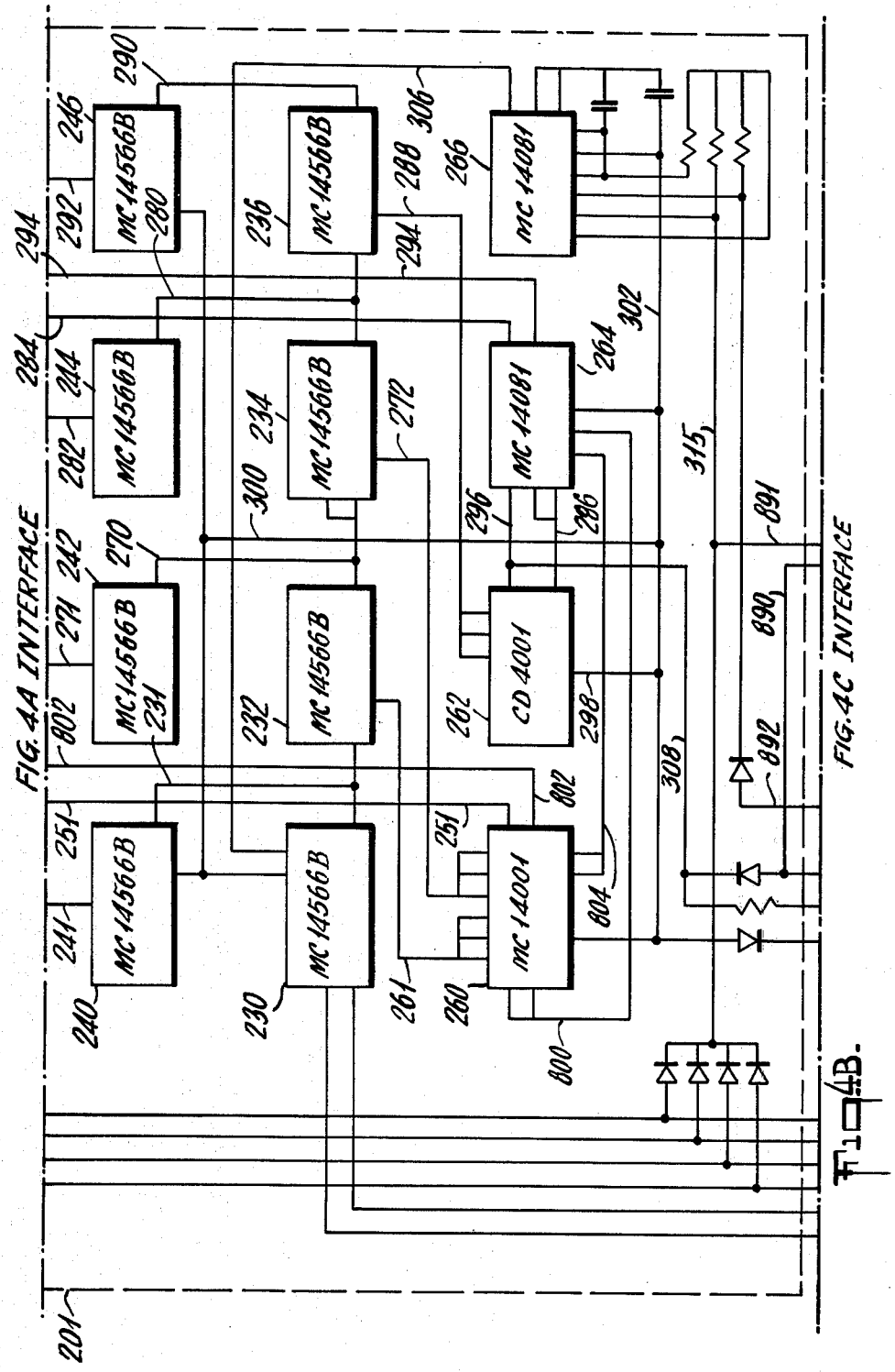

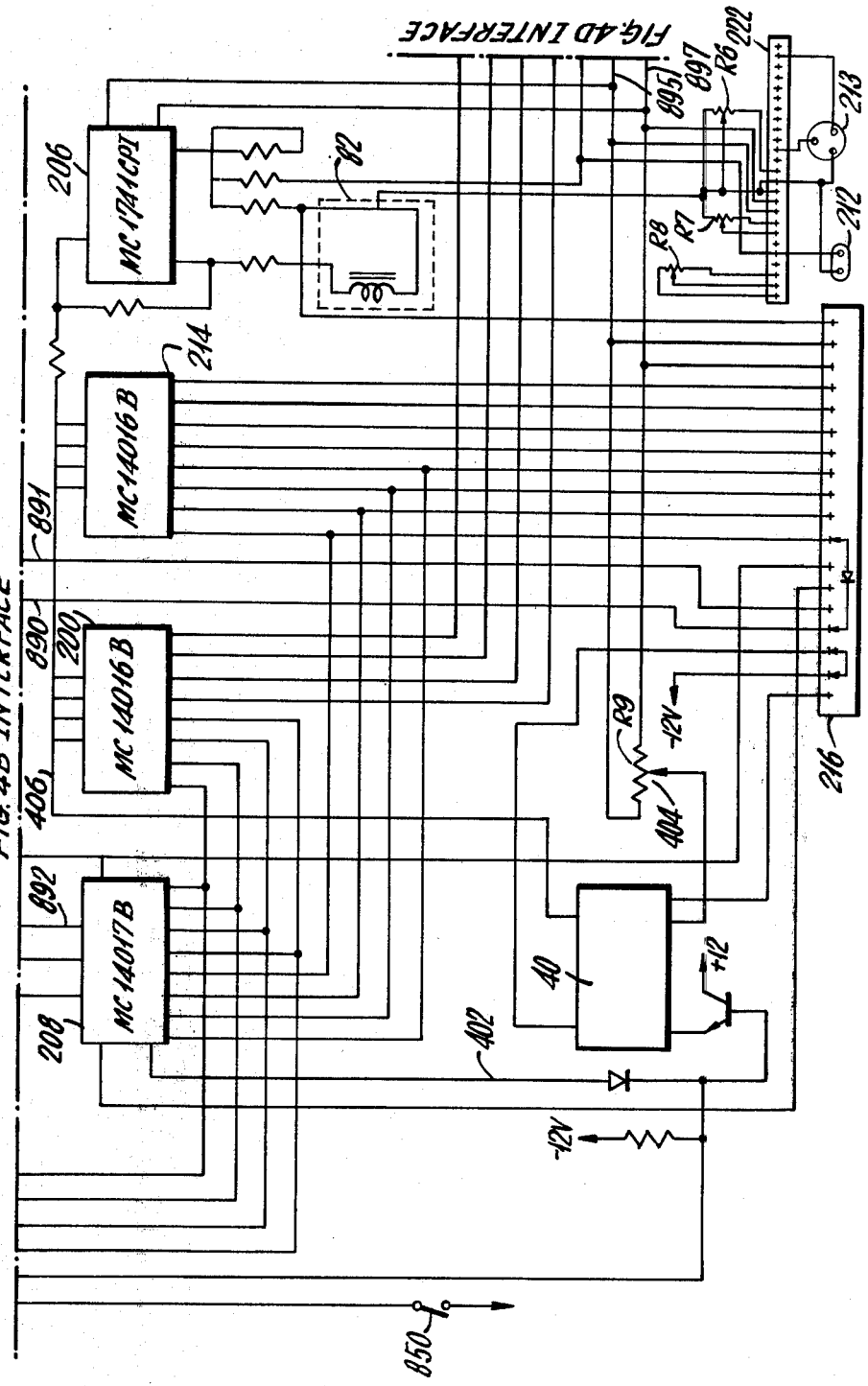

ANALOG-DIGITAL CONTROL DEVICE

BACKGROUND OF THE INVENTION

The present invention relates to an analog-digital control device and more particularly to a control device having a memory with multiple, readily accessible, selectable access ports to allow the control device to be quickly reprogrammed by unskilled personnel and thus render the control device particularly useful for the laboratory environment.

The present invention has found particular application in the field of measuring the absorbency of various absorbent materials of the kind that would be used in disposable diapers, bandages, sanitary napkins, incontinent pads and the like. During use there is often a compression load on such devices, for example, a baby might be sitting on the diaper or a bandage might be wound with some tightness about the body. Therefore, when one is testing the absorbency of a particular material, it is useful to place a compression load on the material and to vary the load according to specific time sequences or other parameters. The absorbency data collected under these conditions will more accurately reflect actual use.

When one is actually testing the absorbency of such material in a laboratory, it is useful to be able to load the material with a prescribed load for a prescribed period of time and to record the data automatically. Especially in the laboratory environment, it is useful to be able to quickly and easily change the applied loads and the time sequences without having to waste valuable laboratory time in resetting the test apparatus.

In the past, such tests had been conducted by a laboratory technician who would place a known weight on a test sample of absorbent material and observe the sample and measure its thickness at regular time intervals. There is a correlation between the thickness and absorbency of the test sample as pointed out in the testing procedure that is employed by a Gravimetric Absorption Tester, described in U.S. patent application Ser. No. 149,214 filed on the same day as this application by Wesley J. McConnell, and assigned to the same assignee of this application. The said McConnell application is incorporated herein by reference.

It would be desirable to have a control circuit for a testing apparatus which would be capable of applying a desired load for a desired period of time and for automatically recording the load actually applied to the sample and for recording the thickness of the sample.

Present analog-digital control circuits are capable of generating a prescribed analog signal for a prescribed variable time periods. Available microprocessor units could be used for such a purpose. However, such microprocessor units are usually sequentially accessible according to a set computer program. If the operator wishes to change any of the input parameters, particularly the prescribed time periods, it is necessary to access the microprocesser at the correct address location, erase existing memory and reprogram the microprocesser according to the new time sequence. This reprogramming can take a significant amount of valuable laboratory time and can usually only be accomplished by a skilled computer programmer.

The time input could also be readily varied by using a number of sequenced timers. This would give ready access to the time input parameter by an unskilled lab technician, but existing timers do not provide for the large variety of time ranges that are sometimes necessary for laboratory applications.

What is needed is a analog-digital control circuit which may be readily and quickly reprogrammed by an unskilled laboratory technician so that test apparatus will have a large variety of input control parameters particularly suited for the laboratory environment.

SUMMARY OF THE INVENTION

The present invention relates to a control apparatus which includes a multi-channel analog memory for storing input analog information and a multi-channel digital memory for storing digital information. Both the analog and the digital memory have multiple, readily accessible and manually selectable access ports so that the control unit may be easily programmed by an unskilled operator. The digital and/or analog information stored in the memory of the control unit can be quickly accessed so that the control unit is well suited for the laboratory environment where the laboratory technician must be able to quickly change input parameters. The input from the digital and analog memories are received by a multiplexing switch which generates a signal representative of the input analog information in accordance with the input digital information. A switching circuit which may be an electronic stepping relay is used for switching the multiplexer from one channel of input to the next in prescribed sequence. An operational amplifier is used to receive the multiplexer output signal and to receive a second signal from an external feedback element. The output of the operational amplifier is representative of the analog information stored in the analog memory compensated by the feedback signal. This output may be used to control an external component.

The present invention uses a special accessing circuit so that the electronic stepping relay will access one channel at a time of the multi-channel digital memory. In the preferred embodiment, the accessing circuit includes a plurality of preset counters, one of which receives a regular timing pulse. Each preset counter is associated with a BCD counter which is used to generate a signal representative of elapsed time. Each BCD counter is associated with a comparator which compares the elapsed time counted by the BCD counter with the programmed time stored on one of the channels of the digital memory. The comparator generates a signal when the time stored on a particular channel of the multi-channel digital memory equals the elapsed time. The accessing circuit also includes a reset and enabling circuit for accessing each channel of the multi-channel digital memory in sequence until all of the information stored in the digital memory has been accessed.

There is circuitry associated with the "stop" button for the control unit which resets the accessing circuit to be in condition to access the first channel of the multi-channel digital memory when it is started again.

The reset and enabling circuit uses, in the preferred embodiment, three latches and a reset generator which receive and store information and issue instructions to various elements of the control unit to carry out the instructions stored in each channel of the digital memory in proper sequence. The preset control unit reset and enabling circuit permits the same preset counter, BCD counter and comparator circuits to be used repeatedly for each channel of the digital memory. Thus the control unit may be smaller and more compact.

The present control circuit includes apparatus for generating a signal when the information stored in memory has been completed so that the operational amplifier can transmit a signal to the external component which is controlled by the control unit to deactivate the external component.

In the preferred embodiment, this control unit is used to control a loading device for testing the absorbency of certain absorbent materials while they are subjected to a load. The present invention incorporates a digital time input and an analog load input which may be easily programmed and reprogrammed by an unskilled operator. All the operator needs to do is to dial in the correct times on each channel of the digital input memory and to dial in the correct loads on each channel of the analog memory and then start the system. There is no need for the operator to have any appreciation of the internal workings of the system nor to have any knowledge of the methods for accessing computers such as microcomputers.

The present invention also includes apparatus for measuring and recording the thickness of the test sample. The control unit also permits the time history of the applied load to be recorded.

BRIEF DESCRIPTION OF THE DRAWINGS

These and other features of the present invention will be more readily appreciated from the following detailed description of the preferred embodiments of the invention taken in conjunction with the following drawings in which:

FIG. 3 shows a schematic representation of major elements of the circuitry of the control apparatus of the present invention;

DETAILED DESCRIPTION OF THE PREFERRED EMBODIMENT

Figure 1:
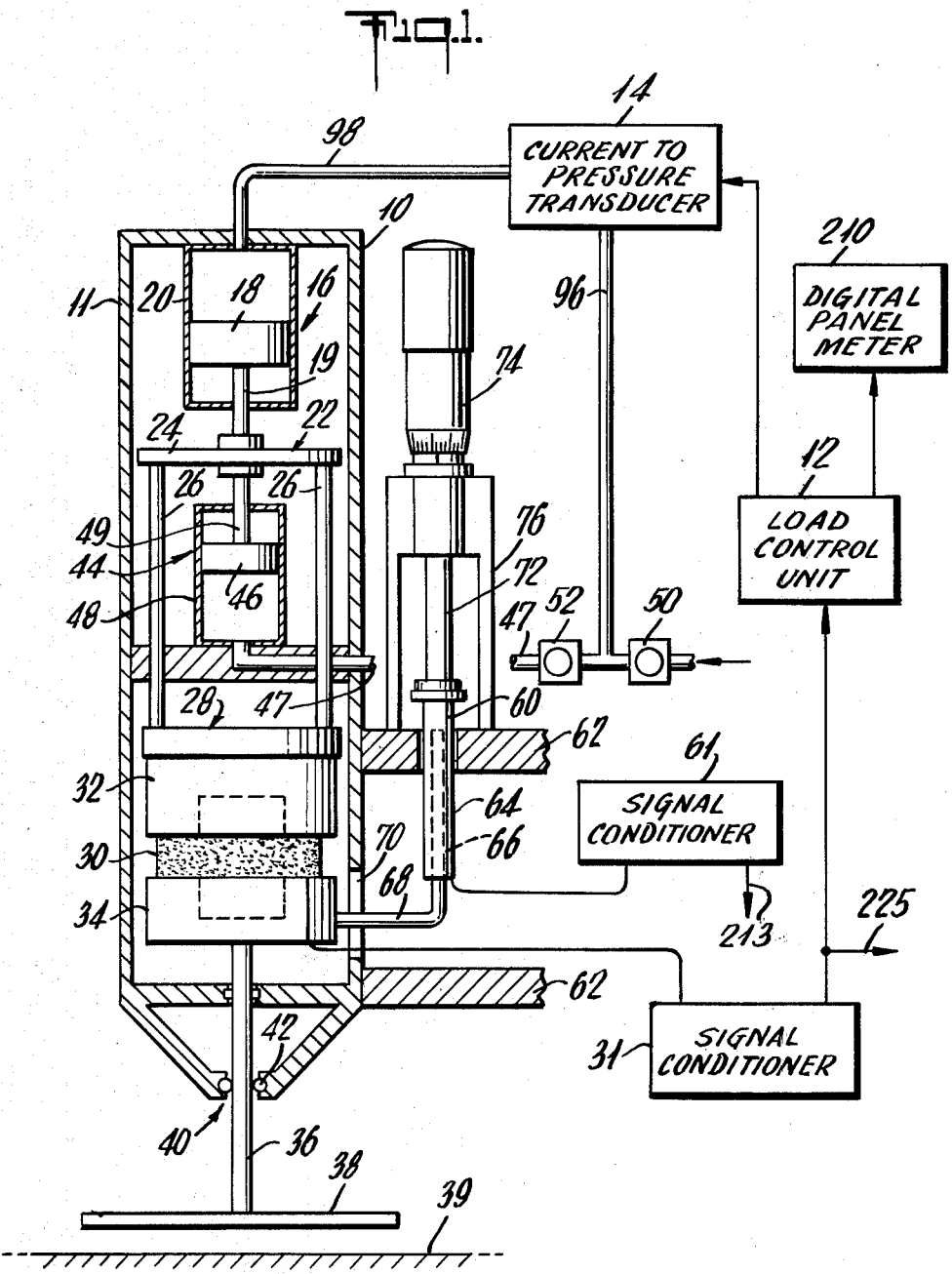
FIG. 1 shows a schematic representation of the loading device in association with which the control apparatus of the present invention is used.

Referring now to FIG. 1, there is shown a sample load device 10 which is controlled by the load control unit 12. Load control unit 12 generates an electrical signal representative of the desired load to be applied to the loading device and transmits that electric signal to a current-to-pressure transducer 14 which converts the electrical signal to a pneumatic output. The pneumatic output is transferred to a first piston actuator 16 comprising a piston 18 moving in cylinder 20 which is rigidly supported on housing 11 of load device 10. The load applied to the upper surface of piston 18 is transferred through piston rod 19 to load transfer assembly 22 which includes a load transfer platform 24 connected by stiff arms 26 to a load cell assembly 28. Load cell assembly 28 includes a force transducer 30 threaded in plastic mountings 32 and 34, which is in turn rigidly connected to output shaft 36, passing through linear ball bushing 42 in guide 40 and terminating in a pressure foot 38 which abuts the test sample (not shown) resting on base plate 39. Thus, the pneumatic load applied to the top of piston 18 is transmitted through the loading device 10 to pressure foot 38. The load applied by foot 38 to the test sample is measured by load cell 30. Load cell 30 is a standard device generally available from a number of manufacturers and which includes two parallelly aligned mounting plates separated by springs having known spring constants. A transformer body is usually mounted on one plate and a transformer core is mounted on the other. The transformer output varies as the plates move toward or away from each other and the transformer core moves into or out of the transformer body in response to a force applied to the load cell. Since the spring constant of the springs separating the two plates is known, and since the transformer output is directly related to the deflection between the two plates, the load cell can be calibrated to read an applied load. A suitable load cell may be purchased from Schaevits Engineering Company of Camden, N.J., Model No. FTA-IT-20. A signal conditioner 31 is used in association with load cell 30 to provide a power supply and to condition the output of load cell 30 to a useful format. As will be subsequently described, the output of load cell 30 is directed to signal conditioner 31 and thence to load control unit 12 and to a recording means.

The loads which are meant to be applied to the test samples are necessarily small and, thus, the data can be affected by the weight of the load transfer apparatus itself, including the moving parts of load device 10, i.e., piston 18, piston rod 19, the load transfer assembly 22, load cell 30 and its mountings 32 and 34, output shaft 36 and pressure foot 38. To compensate for the weight of these parts of loading device 10, the loading device 10 includes an offset counterforce system 44, which includes a piston 46 in a cylinder 48 with a piston rod 49 rigidly connected to load transfer platform 24. Piston 48 is supplied with a constant pneumatic pressure through conduit 47 which urges piston 46 in a direction opposite to that of piston 18 so that load transfer assembly 22 is urged upward with sufficient force to counterbalance the weight of the moving parts of loading device 10. The counterforce assembly 44 presses upwardly with a preset force somewhat greate than the weight of the moving portions of the sample loading device 10. The device is then calibrated so that at zero load, piston 16 presses down with a force equal to or less than the counterforce exerted on piston 46. Light weight materials are used in the loading device as much as possible. The pistons are preferably made of graphite and the cylinders preferably made of glass to reduce friction loading within the cylinders.

As shown in FIG. 1, an air supply is introduced into cylinder 48 through two pressure regulators 50 and 52. These pressure regulators can be purchased from Fairchild Industrial Products Division, Winston Salem, N.C. under Fairchild Pneumatic Pressure Regulator Model 30. Pressure regulator 50 is preferably a 0 to 30 pound pressure regulator which is set to output about 22 pounds per square inch. Pressure regulator 52 is a 0 to 2 pound pressure regulator with an output of about 1.8 pounds per square inch. It can be seen in FIG. 1 that the air pressure supply from the downstream side of pressure regulator 50 is directed to the input of current to pressure transducer 14 and serves as the air pressure supply for cylinder 20. Current-to-pressure transducer 14 will be discussed more thoroughly in connection with FIG. 2 further on in the application.

Still referring to FIG. 1, there is shown a linear variable differential transformer (LVDT) 60 rigidly mounted on a support platform 62 which also supports load device 10. LVDT 60 is used to measure the thickness of the test sample placed on base plate 39, as will be subsequently discussed in greater detail. Transformer body 64 is adjustably mounted on the stem 72 of a vernier 74, vernier 74 is mounted on support 62 by legs 76.

Transformer core 66 is affixed to mounting 34 of load cell 30 by means of an arm 68 which extends through slot 70 in the housing of load device 10.

Figure 4A:
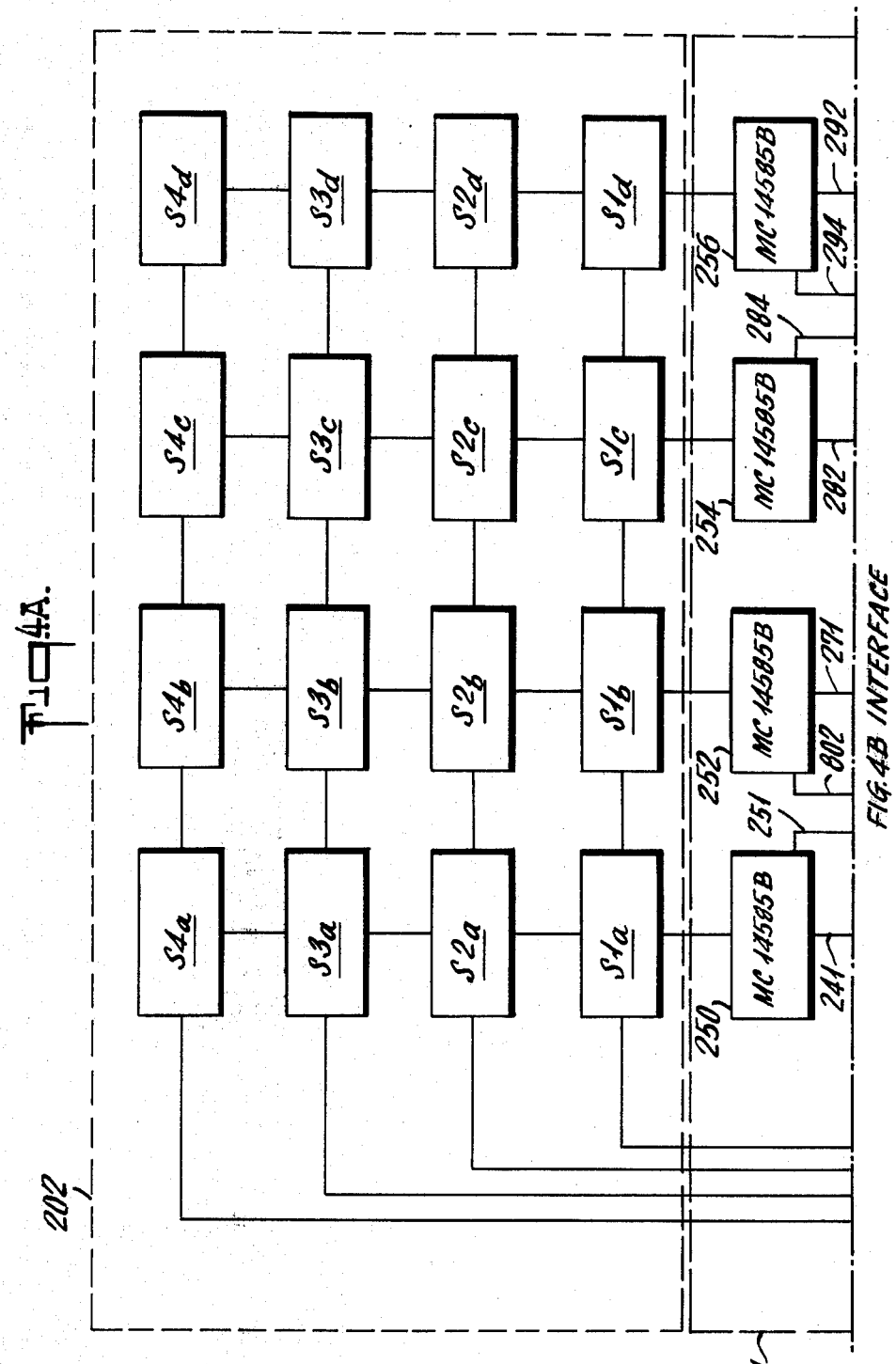
FIGS. 4 A-D show a detailed schematic representation of an electronic circuit of the control apparatus of the present invention. Since the detailed schematic is large, it has been split into four parts A-D, and the interfaces among the various parts are listed on each of the FIGS. 4 A-D; and, FIG. 5 shows a schematic representation of a control panel for the control apparatus of the present invention.

As foot 38 moves up and down according to the variation of thickness of the test sample, load cell support 34, arm 68 and transformer core 66 will correspondingly move, causing core 66 to move with respect to transformer body 60, thus causing the transformer output to vary in accordance with the motion of foot 38. This provides a method of measuring the thickness of a sample that is being subjected to a test. As will be described in further detail in conjunction with FIGS. 4 A–D and the operation of the electronic circuit for load control unit 12, the thickness of a test sample can be monitored and displayed on a digital panel meter 210 and/or recorded on a recording means such as a chart recorder. In order to set the foot at a zero thickness above the surface on which a test sample will be placed, the electronic circuit can be engaged as will be subsequently described, and vernier 74 may be adjusted until the thickness on the digital panel meter reads zero. A signal conditioner 61 is used in association with LVDT 60 to provide a power supply and to condition the output of LVDT 60 to a useful format. As will be subsequently described, the output of LVDT 60 is directed to signal conditioner 61 and thence to a recording means which may be the same recording means as that used for load cell 30.

Figure 2:
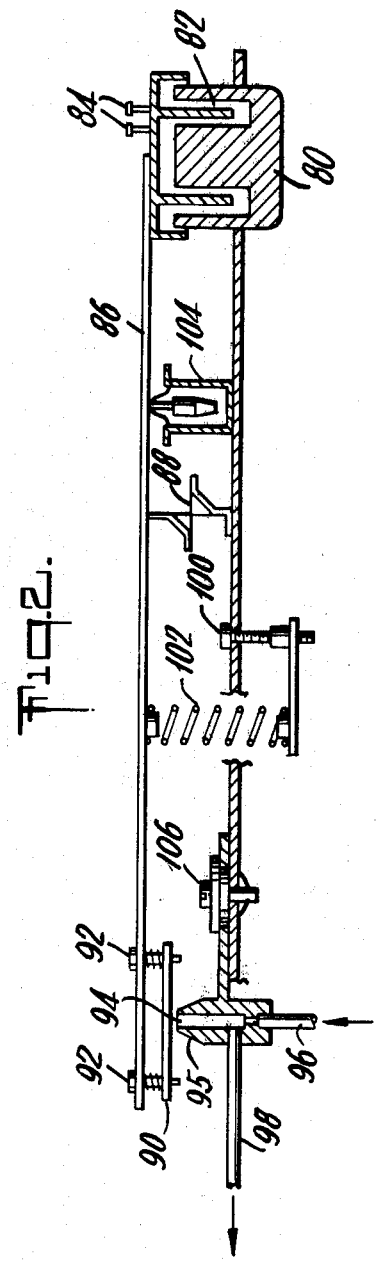
FIG. 2 shows a schematic representation of a transducer used in association with the apparatus of FIG. 1.

The operation of current-to-pressure transducer 14 will now be described in conjunction with FIG. 2. Current-to-pressure transducer 14 is a force-balance instrument that balances an electromagnetic force against a pneumatic force. Transducer 14 includes a permanent magnet 80 and an electrical coil 82. An input signal current is applied to coil 82 through contacts 84. Coil 82 of transducer 14 is mounted on one end of force lever 86 which pivots on flexure pivot 88. An adjustable baffle 90 is mounted on the other end of lever 86 which may be adjusted by means of spring loaded screws 92. Transducer coil 82 is suspended in the gap of permanent magnet 80. As the current flow through transducer coil 82 increases, the coil moves up out of the gap of magnet 80, raising the coil end of force lever 86 and lowering baffle 90 against orifice 94 of nozzle 95, directing the air supply from input line 96 to output line 98 and into cylinder 20 of load device 10. As the input signal current to the transducer coil decreases, the coil moves down into the gap of magnet 80 and raises baffle 90 out of engagement with nozzle 95 to permit the air supply from input line 96 to vent to the atmosphere, thus reducing the amount of pressure directed through output line 96 into cylinder 20. A zero-adjustment screw 100 is provided to compress zero-adjustment spring 102. Zero adjustment 100 may be adjusted together with pressure regulator 52 to insure that when a "zero" load signal is delivered to transducer 14, that the air in cylinder 44 is sufficient to overcome the air pressure in cylinder 20 and the weight of the moving parts of load unit 10, so that when "zero" load exists foot 38 will automatically rise from base plate 39. Damper 104 is provided. A span adjustment 106 is provided to position nozzle 95 in relation to pivot 88. Span adjustment 106 is provided by a pair of screwdriver adjusted cams which can slide the nozzle axially of force lever 86. Thus current-to-pressure transducer 14 will convert the output of load control unit 12 to a pneumatic output for introducing a load into cylinder 20 which will be delivered through the apparatus of load device 10 to foot 38 and to the test sample. Load cell 30 provides a feedback to load-control unit 12 to insure that the desired applied load is properly adjusted and maintained at the required level and will not drift from that required level.

The major elements of the circuitry of load-control unit 12 will now be discussed in conjunction with FIG. 3 and the circuitry of load-control unit 12 will be specifically discussed in detail in connection with FIGS. 4 A–D.

Referring now to FIG. 3, there is shown a schematic representation of the major elements of the circuitry of the load-control unit 12. Functional groups of components and their interrelations will be discussed first. Then the detailed operation of each functional group will be discussed in conjunction with the circuit diagram shown in FIGS. 4 A–D.

Four-position automatic multiplexer switch 200 receives digital input, for example a time sequence, from a multi-channel digital input device 202. Switch 200 also receives analog input, for example a voltage representative of a desired load to be applied to loading device 10, from multi-channel analog input device 204. Switch 200 operates to apply the analog signal received over the first analog input channel for a period of time received from the first digital input channel to a comparator 206. Comparator 206 compares the desired analog input signal, for example load, with the load measured by load cell 30 and generates a signal to the coil 82 of current-to-pressure transducer 14 representative of the desired load. Load unit 12 includes an accessing circuit 201 and a switching circuit 208 which are operatively connected to switch 200 and to multichannel digital input 202 to automatically access the different channels of digital input 202 and analog input 204 in sequence. The load-control unit 12 includes a digital panel meter display unit 210 on which the load applied by foot 38 to the test sample may be displayed. The load unit 12 is equipped with suitable connection means 212 (see FIG. 4C) for a recorder, so that the load applied to foot 38 of load device 10 may be recorded as a function of the digital input signal on a continuous basis, for example, on a chart recorder or other well known recording means.

In this preferred embodiment, both the digital input 202 and the analog input 204 operate on four channels. Each channel of analog unit 204 stores a particular load value. Each channel of digital device stores a particular time value. Thus four different loads may be applied for four different time periods. Switch 208 is an electronic stepping relay 208 and is an eight-channel device which employs only four of its eight channels for this preferred embodiment. Load unit 12 also includes a second automatic multiplexer switch 214 (see FIG. 4C) which is capable of receiving digital information from the four unused channels of electronic stepping relay 208 and of receiving analog input from a function generator (not shown) which may be connected into the load control unit 12 through the appropriate pin connections of printed circuit board jack 216 (see FIG. 4C). Thus, instead of being confined to using a simple time sequence digital input, the present invention is capable of receiving any digital input, for example, ramp functions or even oscillating functions. Automatic switches 200 and 214, comparator 206 and electronic stepping relay 208 are all pin-connection integrated circuits. Switches 200 and 214 are analog switch/multiplexers Model No. MC1406B available from Motorola Company, and the specification sheets of those devices are hereby incorporated by reference in this application. Electronic stepping relay 208 is a decade counter/divider Model No. MC14017B available from Motorola Company, and the specification sheets of that device are incorporated by reference herein. Comparator 206 is an operational amplifier Model No. MC1741CPI from the Motorola Company, and the specification sheets for that device are incorporated by reference herein.

Digital panel meter 210 is available on the open market from Weston Instruments, a Division of Sangamo Weston, Inc. of Newark, N.J. under Model No. 1234.

The components of multi-channel digital input device 202 multi-channel analog input device 204 and accessing unit 201 and their operation will now be discussed. Digital device 202 has four memory channels each with four modes of operation corresponding to seconds, ten second intervals, minutes and ten minute intervals. The four switching units for the four modes of the first channel of device 202 are $S1_a$, $S1_b$, $S1_c$ and $S1_d$. The four units of the second channel are $S2_a$, $S2_b$, $S2_c$ and $S2_d$ (see FIG. 4A). The units of the third channel are $S3_a$, $S3_b$, $S3_c$ and $S3_d$. The units of the fourth channel are $S4_a$, $S4_b$, $S4_c$ and $S4_d$. Each one of these memory units is a thumb-wheel switch which may be purchased from Inter-Market, Inc. of Glenview, Ill. 60025, Model No. MF-21A. These are ten-position BCD extended board switches. The units of each channel are ganged together as a set. In this preferred embodiment, the digital input is timed so that in order to program the memory of the digital device 202, one need only dial in the prescribed time for which it is desired to have each channel operate. For example, the first channel may operate for ten minutes, the second channel may operate for nine minutes and thirty-five seconds and so on. The first unit in each channel, namely $S1_a$, $S2_a$, $S3_a$ and $S4_a$, stores information in seconds. The second unit in each channel, namely $S1_b$, $S2_b$, $S3_b$ and $S4_b$, stores information in ten second intervals. The third unit in each channel, namely $S1_c$, $S2_c$, $S3_c$ and $S4_c$, stores information in minutes. The fourth unit in each channel, namely $S1_d$, $S2_d$, $S3_d$ and $S4_d$, stores information in ten minute intervals. Thus, on each channel a period of time equal to 99 minutes and 99 seconds may be entered.

Analog input device 204 has four memory channels represented by four sets of ten-turn potentiometers of the kind available from Bourns of Mexico No. 7923M. Each channel includes two set ranges. In this preferred embodiment analog device 204 stores values equivalent to the load to be applied by foot 38 against a test sample and the first of each set range corresponding to an output of 1–1,000 grams and the second of each set range corresponding to an output of 1,000–10,000 grams. Two set ranges are required because it is difficult to obtain a device which has a linear response over such a broad range of outputs. Each channel has a separate switch, respectively, S5, S6, S7 and S8, for selecting the upper or lower set range (see FIG. 4D). Once the set range is chosen, the value of the applied analog signal within that range is determined by using ten-turn potentiometers R1, R2, R3 and R4, respectively.

Accessing unit 201 (see FIGS. 4A & B) permits the separate channels and modes of device 202 to be accessed in sequence and includes four preset counters 230, 232, 234 and 236; four BCD counters 240, 242, 244 and 246; four comparators 250, 252, 254 and 256; and, an enable and reset circuit including latches 260, 262, 264 and reset generator 266. Preset counters 230, 232, 234 and 236 which are pin-connection integrated circuit time-base generators Model No. Mc14566B, available from Motorola Company. The specification sheets of those devices are incorporated by reference herein. Preset counter 230 is preset to issue a pulse every tenth of a second. Preset counter 232 is preset to issue a pulse every ten seconds. Preset counter 234 is preset to issue a pulse every one minute, and preset counter 236 is preset to issue a pulse every ten minutes.

Preset counter 230 receives an input of regular pulses. In this preferred embodiment the regular pulse input is taken directly from an alternating current line available at the facility where the device is being used. Alternatively, an oscillator could be used. The line pulse may be introduced into preset counter 230 at one input terminal of the pin-connection integrated circuit. Preset counter 230 is adapted to receive either 60 cycle or 50 cycle house current. If 60 cycle current is applied to preset counter 230, switch 850 on back panel of the housing for control unit 12 is left open. If 50 cycle current is applied, switch 850 is closed to ground part of the internal circuitry of preset counter 230 and permit that internal circuitry to compensate for the 50 cycle current.

Pulses emanating from preset counters 230, 232, 234 and 236 are introduced in the proper sequence to BCD counters 240, 242, 244 and 246 which are also pin-connection integrated circuit units Model Nos. MC14566B available from Motorola Company, and the specification sheets of this device are incorporated by reference herein. BDC counters 240, 242, 244 and 246 count the pulses received from preset counters 230, 232, 234 and 236 and issue pulses representative of elapsed time to comparators 250, 252, 254 and 256, respectively, which comparators compare the elapsed time signal received from BCD counters 240, 242, 244 and 246 with the programmed time stored in the thumb-wheel switches of unit 202. When the elapsed time equals the programmed time, each comparator issues a signal to an appropriate unit of an enable-and-reset circuit which includes latches 260, 262, 264 and reset generator 266. Latch 260 is a Nor Gate Model No. MC14001B available from Motorola Company, and the specification sheets of that device are incorporated by reference herein. Latch 262 is Nor Gate Model No. CD4001 available from Motorola Company, and the specification sheets of that device are incorporated by reference herein. Latch 264 and reset generator 266 are both And Gates Model No. MC14081 available from Motorola Company, and the specification sheets of that device are incorporated by reference herein.

The operation of accessing unit 201 and its components preset counter units 230, 232, 234 and 236, BCD counter units 240, 242, 244 and 246, comparator units 250, 252, 254 and 256 and enable-and-reset circuit, including latches 260, 262 and 264 and reset generator 266, will now be described in detail. When load control unit 12 is turned on, relay 208 has been preconditioned to monitor the first channel of digital input device 202

(switches S1$_a$, S1$_b$, S1$_c$ and S1$_d$) and analog unit 204, as will be subsequently described in greater detail in connection with the operation of "start" switch S10 and "stop" switch S9 (see FIG. 4D). Reset generator 266 receives information over line 315 (see FIG. 4B) that one of the channels of digital input device 202 is being accessed and is thus ready to receive further information about the status of accessing unit 201 so that it can issue reset instructions to relay 208 when needed so that it will access subsequent channels of input devices 202 and 204.

Input pulses are introduced to preset counter 230 and, when pulses have been counted amounting to the preset value on the counter of one second, a signal is issued to BCD counter 240 over line 231. BCD counter 240 counts pulses received from preset counter 230 to accumulate an elapsed time and issues signals over line 241 to comparator 250, which compares the elapsed time received from BCD counter 240 with the times stored in memory corresponding to the times set on switch S1a. When the elapsed time equals the set time, comparator 250 issues a signal over line 251 to latch 260. Latch 260 then issues a pulse over line 261 to reset preset counter 232 to "zero" and enable it to start counting input pulses at its preset value of ten second intervals. Latch 260 also informs latch 264 over line 800 that the sequence specified on the first unit S1a. has been completed and latch 264 stores that information. Preset counter 232 then issues pulses every ten second intervals to BCD counter 242 over line 270, and BCD counter 242 counts those pulses and issues an elapsed time signal over line 271 to comparator 252 which compares it with the time stored in memory on the second unit of S1$_b$ of the first channel of memory. When elapsed time equals the time stored in memory, comparator 252 issues a signal to latch 260 over line 802. Latch 260 then issues a signal over line 272 which enables preset counter 234 to start counting at its preset interval of one minute. Latch 260 also informs latch 264 over line 804 that the instructions from the second unit S1$_b$ of the first channel of memory have been completed, and latch 264 stores that information.

Preset counter 234 issues pulses at one minute intervals over line 280 to BCD counter 244, which issues an elapsed time signal over line 282 to comparator 254, which compares elapsed time with the time stored in the third unit S1$_c$ of the first channel of memory. When elapsed time equals the time stored in S1$_c$, comparator 254 informs latch 264 over line 284 that the instructions on the third unit of the first channel of memory have been completed. Latch 264 then informs latch 262 of that fact over line 286. Latch 262 then enables preset counter 236 to start counting at its preset time interval of ten minutes by issuing a signal over line 288.

Preset counter 236 issues pulses at ten-minute intervals to BCD counter 246 over line 290, which in turn issues elapsed time pulses over line 292 to comparator 256 which compares the elapsed time with the time set on the fourth unit, S1$_d$ of the first channel of memory. When elapsed time equals the time set on the fourth unit S1$_d$, comparator 256 informs latch 264 of that fact over line 294. Latch 264 informs latch 262 of the completion of the instructions in the fourth unit of the first channel of memory over line 296. Latch 262 then informs reset generator 266 over lines 298 and 302 that the instructions in the fourth unit of the first channel of memory have been completed and reset generator 266 is enabled to operate. Reset generator 266 operates for only one-tenth of a second because it is connected over line 306 to preset counter 230. Preset counter 230 is configured like a clock to generate both one second and one-tenth of a second information. Line 306 connects to the one-tenth of a second output of preset counter 230. Reset generator 266 issues an instruction over line 302 to electronic stepping-relay 208 causing it to step to the next step and monitor the second memory channel of digital input device 202 and switches S2$_a$, S2$_b$, S2$_c$ and S2$_d$. The pulse issued by reset generator 266 over line 302 to stepping relay 208 also resets latches 260, 262, and 264 to be ready to access the second channel of digital input device 202. The same reset pulse also travels over line 300 to reset preset counter 230 and BCD counters 240, 242, 244 and 246 so that they are ready to access the second channel of digital input device 202. This pulse to preset counter 230 also has the advantage of turning off preset counter 230 during the one-tenth of a second that reset counter 266 is enabled so that preset counter 230 does not get ahead of sequence during the one-tenth of a second it takes to reset the circuit and switch from the first channel to the second channel of digital input device 202.

Once stepping relay 208 has been reset and preset counters 230 and BCD counters 240, 242, 244 and 246 have been reset, digital input device 202 is enabled to access the second channel of memory, represented by switches S2$_a$, S2$_b$, S2$_c$ and S2$_d$, and the process repeats itself as above described. When the fourth channel of memory has been accessed and completed, stepping relay 208 tries to step to the next step. It is, however, wired internatively to shut itself off. When this occurs, stepping relay 208 enables relay 400 (see FIG. 4C) over line 402, which causes a signal to be drawn from potentiometer 404 to introduce a signal to comparator 206 over line 406. This causes comparator 206 to generate a signal to coil 82 of current-to-pressure transducer 14, which completely opens baffle 90 away from nozzle 95 and bleeds off the supply of air to cylinder 20 of load device 10. The air supply directed to cylinder 48 against piston 46 of counterbalance unit 44 is then sufficient to overcome the weight of the moving parts of load unit 10 and raise foot 38. Thus, when load unit 12 has completed its sequence, load unit 12 shuts itself off and raises foot 38.

We have now identified the major elements of load unit 12 in connection with FIG. 3 and described their operation in connection with FIGS. 4 A-D. We have explained how multiplexer 200 received pre-programmed information from digital input 202 and analog input 204 and delivers an output signal to comparator 206 which compares it with the signal received from load cell 30 and generates a signal representative of desired load to transducer 14. The sequence by which accessing unit 201 accesses the desired channels of input devices 202 and 204 and steps relay 208 has been described in detail. Next we will describe the circuitry for monitoring the thickness of a test sample. Then we will describe the control panel for the load control unit and the method of programming the unit. Lastly, we will describe the circuitry associated with the "start" and "stop" buttons S10 and S9, respectively.

Load-control unit 12 also includes the capability of displaying and recording the thickness of the test sample as a function of time. Linear variable differential transformer (LVDT) 60 and signal conditioner 61 is adapted for connection to printed circuit board jack 220 (see FIG. 4D) and thence through appropriate circuitry to a switch 218 which is operatively connected to digital panel meter 210. Switch 208 is operative in one position to connect digital panel meter 210 to load cell 30 through printed circuit board jack 222 where it will monitor output of load cell 30 or to LVDT 60 through printed circuit board jack 220 where it will monitor the output of LVDT 60. Jack 222 incorporates a jack 213 for receiving the output of load cell 30 and its signal conditioner 31 and a jack 212 for connection to a recorder, like a chart recorder (not shown) to continuously record the output of load cell 30.

Printed circuit board jack 220 also incorporates jacks 225 for receiving the output from LVDT 60 and its signal condition 61 and jacks 224 for connecting a recorder, like a chart recorder (not shown), to continuously record the output of LVDT 60, calibrated to the thickness of the test sample, as a function of time. Thus it can be seen that both the load which is applied to the test sample and the thickness of the test sample may be continuously recorded automatically as a function of time. A single recorder can be used if desired. According to the desires of the operator, the digital panel meter may be connected to display either the output of load cell 30 or the output of LVDT 60.

Thickness selection unit 221 also incorporates a series of switches connected in four parallel branches to allow the thickness range over which LVDT 60 takes measurements to be varied according to the thickness of the sample. And incorporates a series of four gang switches, S13, S14, S15 and S16, which are representative of thickness ranges from 0–1 inch for S13, 0–0.05 inches for S14, 0–0.2 inches for S15 and 0–0.1 inches for S16.

Figure 5:
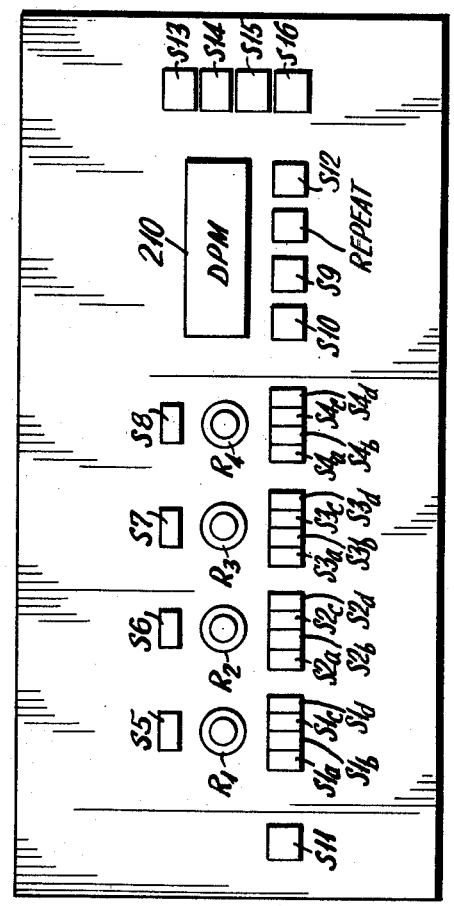

Referring now to FIG. 5, there is shown the front control panel of the load unit 12. A main power switch S11 is used to turn the system on and to energize its components. S11 is shown also in FIG. 4D. Thumb-wheel switches for each channel of digital input device 202 are ganged together in units of four, the first gang corresponding to switches $S1_a$, $S1_b$, $S1_c$ and $S1_1$. Similar gangs are provided for the S2 channel, the S3 channel and the S4 channel. Above each gang of thumb-wheel switches is a knob which operates ten-position potentiometers R1, R2, R3 and R4 of analog input device 204. Above each potentiometer knob is another switch corresponding to the set range switches $S_5$, $S_6$, $S_7$ and $S_8$ for each channel of analog unit 204. Proceeding from left to right in FIG. 5, one encounters digital panel meter 210. Under digital panel meter 210 is a "start" switch S10, a "stop" switch S9 and meter switch S12. A blank is left for a "repeat" button which would direct the unit through its sequence a second time if desired. Also included on the front panel are a set of four switches ganged together corresponding to switches S13, S14, S15 and S16 to set the thickness range for the LVDT 60.

The procedure for programming the load control unit 12 will now be discussed. First, the load control unit will be programmed for load and then for thickness.

First, the supply of air pressure is turned on to supply cylinders 20 and 48 through pressure-reducing valves 50 and 52. The operator then moves digital panel meter select switch S12 to the "load" position so that digital panel meter 210 displaces the load sensed by load cell 30. "Zero" load should appear on the digital panel meter. Certain electronic drift from "zero" may be experienced. If the system is far from "zero" when no load is being applied corrections can be made by opening the control unit 12 to gain access to variable resistors R6, R7 and R8. The operator then sets each memory channel of digital input device 202 to read "30 seconds" in order to give sufficient time for the operator to introduce the desired load to analog input device 204. The load range is then chosen for each of the four channels of analog input device 204 by setting switches S5, S6, S7 and S8 either to the 0–1,000 gram level or to the 1,000–10,000 gram level. The operator then presses the "start" button, and the foot 38 will come down and hit the base plate 39. A number corresponding to the load applied by foot 38 to base plate 39 will be displayed on digital panel meter 210. The operator then adjusts the ten-turn potentiometer R1 for the first channel of analog input device 204 until the desired reading appears on the digital panel meter. The operator has a 30-second period in which to make this entry. A longer time may be used if it is believed necessary.

After the 30 seconds for programming the desired load into the first channel of analog input device 204 have elapsed, the load unit 12 will switch to the second channel for a period of 30 seconds, which will permit the operator to introduce the second desired load onto the second channel of analog input device 204 by adjusting potentiometer R2. The operator continues this sequence until all four channels of analog input device 204 have been programmed.

After the desired loads have been entered into analog input device 204, the operator dials in the desired time to digital input device 202 by turning thumbwheel switches $S_1$, $S_2$, $S_3$ and $S_4$ to the desired values.

The operator then sets load unit 12 for the desired thickness level as follows. The desired time periods are dialed in on the thumb-wheel switches to each channel of digital input device 202. The operator hits "start" button S10, and foot 38 starts to come down into position toward base 39. Digital panel select switch S12 is then switched to the thickness mode so that digital panel meter 210 displays thickness measured by LVDT 60. The operator then selects the desired thickness range, for example the full scale range can be set to 0–1 inches by energizing switch S16. With foot 38 down flat on base 39, vernier 74 is adjusted until LVDT 60 displays a thickness of "zero" on digital panel meter 210. The operator then hits the "stop" button S9 to lift foot 38 so that the test sample may be placed on base 39 under foot 38. The operator then hits start button S10 again, and foot 38 will come down and engage the test sample with a preselected load, and load unit 12 will measure the thickness of the test sample under this load and will also measure the thickness of the test sample on a continuous basis as it collapses or expands during the test as it absorbs water. As previously mentioned, a chart recorder (not shown) may be connected to recorder hook-up 224 in printed circuit jack 220 so that the time history of the thickness of the sample may be recorded. Similarly, a second chart recorder can be connected to recorder jack 212 of printed circuit board jack 222 to record a time history of the applied load. Alternatively, one recorder with two inputs may be used.

Figure 4D:
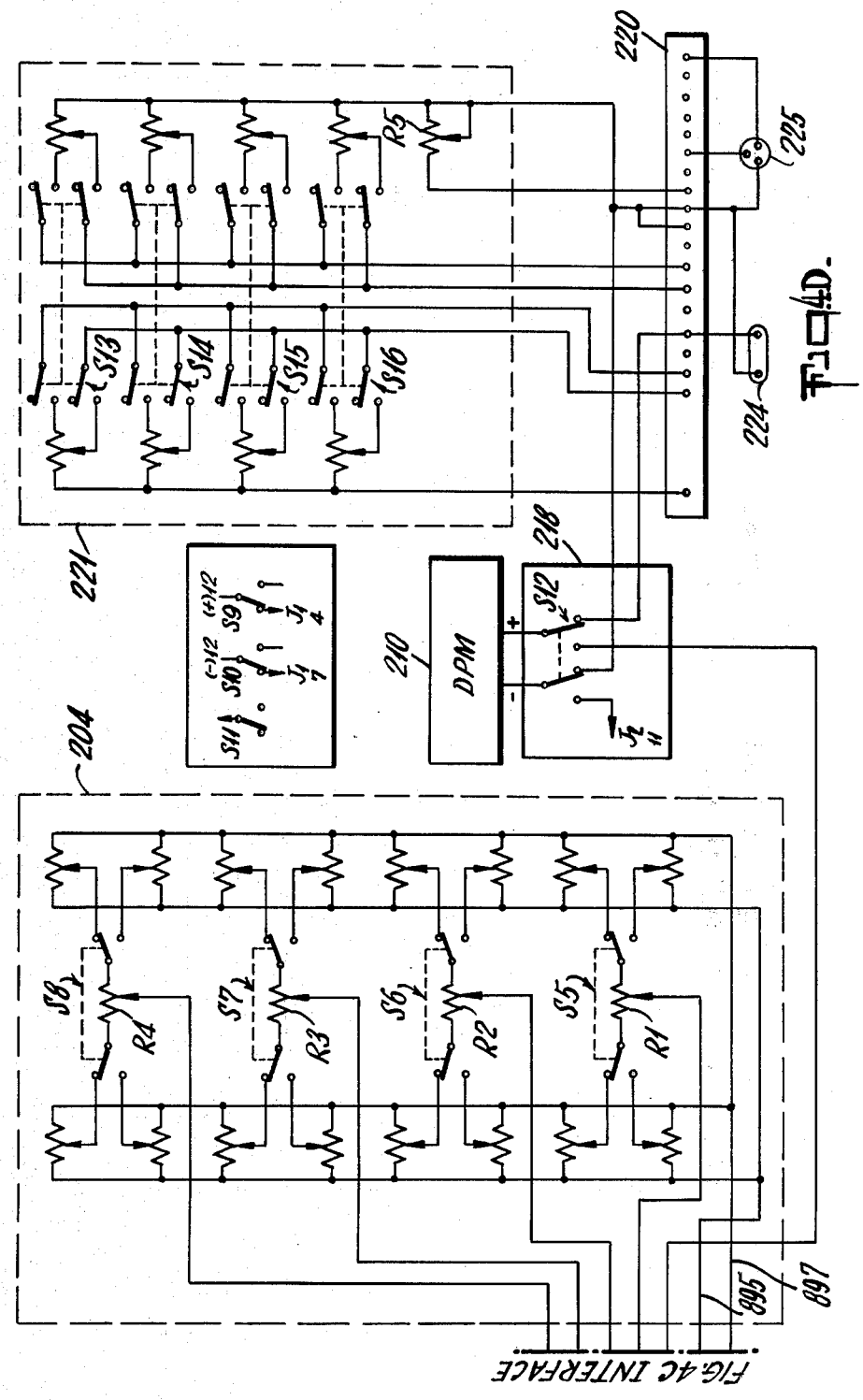

It can be seen from FIG. 4D that the "start" button S10 is connected between a negative voltage of 12 volts and pin 7 of printed circuit board jack 216 so that when the "start" button is engaged, a negative voltage is impressed upon the clock input of electronic stepping relay 208 which starts stepping relay 208, causing it to monitor the first channel of digital input device 202 and correspondingly the first channel of analog input device 204 so that load unit 12 starts through its sequence.

It will be noted that "stop" switch S9 is connected between a positive voltage of 12 volts and pin number 4 of printed circuit board jack 216, so that as the "stop" switch is engaged, a positive voltage is used to reset electronic stepping relay 208, which in turn sets the relay 208 to "zero", thus, enabling relay 400 to be in the conductive condition sending a signal from potentiometer 404 through relay 400 over line 406 to comparator 206 to raise foot 38.

Also, when "stop" button S9 is engaged, a signal is sent over line 308 to enable latch 262 to send a signal over line 298 and 300 to reset preset counter 230 and BCD counters 240, 242, 244 and 246. At the same time a signal is sent over line 302 to enable the reset generator 266. Reset generator 266 then steps stepping relay 208, which in turn enables relay 400 to send a signal from potentiometer 404 through relay 400 over line 406 to comparator 206 to raise foot 38. Thus, when the "stop" button is hit, the foot is raised, and the first preset counter 230 and all of the BCD counters 240, 242, 244 and 246 are reset and ready to begin counting from the initial condition when the "start" button is engaged the next time.

It can be seen that the present invention provides a control circuit for load device 10, which incorporates a digital time input and an analog load input which may be easily programmed and reprogrammed by an unskilled operator. All that the operator needs to do is dial in the correct times on each channel of the digital input device 202 and to dial in the correct loads on the analog input device 204 and then start the system. There is no need for the operator to have any appreciation of the internal workings of the system nor to have any knowledge of the methods of accessing computers such as microcomputers. The present control unit reset and enabling circuits, latches 260, 262, and 264 and reset generator 266 permit the same preset counter, BCD counter and comparator circuits to be used repeatedly for each channel of digital input memory, so that digital input device 202 can be small and compact. The apparatus is designed to operate either on a pulse derived directly from an alternating current line source or from a pulse generator. The reset and enable circuit is carefully designed to shut off the preset counters during the time when the electronic stepping relay is being reset, so that the digital input device 202 does not get even a tenth of a second out of sequence as it accesses through the multiple channels of memory.

Load unit 12 is flexibly designed to incorporate a function generator in memory rather than merely a time sequence. Time sequence memory is stored on the thumbwheel switches. The function generator digital input may be introduced through printed circuit board 216 using switch 214 instead of switch 200. Switch 214 is flexibly designed to be coupled directly to stepping relay 208, so that it may receive a timed digital input and a function analog input. Alternatively, it may be coupled directly to a digital functional input and an analog functional input. This provides a great deal of flexibility to load control circuit 12.

In this preferred embodiment, load control circuit 12 has been used to operate load device 10. However, it will be clear to those skilled in the art that this control unit is useful to control any analog parameter according to any digital input function. While this invention has been described in conjunction with certain preferred embodiments, those skilled in the art will appreciate that many changes and modifications may be made to the preferred embodiment without departing from the scope of the invention. Thus, it is not intended that the scope of the invention be limited except as set forth in the following claims.

I claim:

1. A control apparatus comprising:
   multi-channel analog memory means for storing input analog information and having multiple, readily accessible, manually selectable access ports;
   multi-channel digital memory means for storing input digital information and having multiple, readily accessible, manually selectable access ports;
   multiplexer means adapted to receive input analog information from said multi-channel analog means and input digital information from said multi-channel digital means and to generate a signal representative of said input analog information in accordance with said input digital information;
   switching means for switching said multiplexer means from one channel of input to the next in prescribed sequence; and,
   operational amplifier means for receiving a first signal from said multiplexer means and for receiving a second signal from an external feedback element, and for generating an outlet signal representative of said analog information compensated by said feedback signal to an external component.

2. The apparatus of claim 1 further including means for accessing said multi-channel digital memory means one channel at a time in desired sequence.

3. The apparatus of claim 2 wherein each channel of said multi-channel digital memory means includes a plurality of modes each corresponding to a time interval and said accessing means includes:
   a plurality of preset counter means each operatively associated with one of said modes and preset to count a time interval corresponding to its associated mode;
   pulsing means for delivering a regular pulse signal to said preset counter means;
   a plurality of BCD counter means each operatively associated with one of said preset counter means and adapted to receive signals from its associated preset counter means at said preset time intervals and to generate a signal representative of elapsed time;
   a plurality of comparator means, each operatively associated with one of said BCD counter means and each also operatively associated with one mode of each channel of said multi-channel digital memory means, for generating a signal when the time stored on its associated mode of the operative channel of said multi-channel digital memory means equals elapsed time;
   a reset and enabling means for accessing each channel of said multi-channel digital memory means in sequence and for enabling each mode of each digital channel in sequence until all of the input information contained in said digital memory means has been completed.

4. The apparatus of claim 2 further including repeat means for instructing said accessing means to access the information contained in said analog memory means and said digital memory means again.

5. The apparatus of claim 2 further including means for introducing a stop signal at any time and thereby resetting said accessing means to be in condition to access the first channel and the first mode of said multi-channel digital memory means when said apparatus is started again.

6. The apparatus of claim 2 further including means for introducing a start signal to cause said switching means to access said first channel of said multi-channel digital memory means.

7. The apparatus of claim 3 wherein said reset and enabling means includes:
first, second and third latching means and a reset generator means;
said first latching means adapted to receive a signal from said first mode comparator means and to generate a signal informing said third latching means that said first mode has been completed and for generating a second signal to reset said second mode preset counter means to enable it to start counting;
said first latching means adapted to receive a signal from said second mode comparator means and to generate a signal to inform said third latching means that said second mode has been completed and to generate a second signal to reset said third preset counter means to enable it to start counting;
said third latching means adapted to receive a signal from said third mode comparator means and to generate a signal informing said second latching means that said third mode has been completed to thereby enable said second latching means to send a reset signal to said fourth preset counter means to enable it to start counting;
said third latching means adapted to receive a signal from said fourth comparator means and to generate a signal informing said second latching means that said fourth mode has been completed and thereby enabling said second latching means to enable said reset generator to reset said BCD counter means and said first preset counter means and to reset said switching means to zero, all with a single pulse from said reset generator means.

8. The apparatus of claim 7 wherein said reset generator means is operatively connected to said first preset counter means so that when said reset generator means is enabled, it will generate a signal of a duration equal to the time interval on said first preset counter means;
said reset signal operative to switch said switching means to access the next channel of said multi-channel digital memory means in sequence.

9. The apparatus of claim 7 wherein said first and second latching means are Nor Gates and said third latching means and said reset generator means are And Gates.

10. The apparatus of claim 8 further including:
means for generating a completion signal to said operational amplifier means;
means associated with said switching means to prevent said switching means from switching after accessing of the last channel of multi-channel digital memory means has been completed and for generating a signal corresponding to that condition; relay means responsive to said corresponding signal, for selectably connecting said completion signal means to said operational amplifier means in response to said corresponding signal.

11. The apparatus of claim 1 further including digital panel meter display means for displaying the signal sent from said operational amplifier means to said external component.

12. The apparatus of claim 11 further including means for measuring the distance between a surface of said external component and a test surface.

13. The apparatus of claim 12 wherein said means for measuring the distance between a surface of said external component and a test surface include a linear variable differential transducer.

14. The apparatus of claim 13 further including switching means adapted to selectively permit the output of said linear variable differential transducer or said operational amplifier means to be displayed on said digital panel meter means.

15. The apparatus of claim 1 wherein the signal generated by said multiplexer means represents load and said external feedback component includes a load cell for measuring a load applied to a test sample.

16. The apparatus of claim 1 further including recording means operatively associated with said operational amplifier means for recording the signal generated by said operational amplifier means to said external component.

17. The apparatus of claim 1 further including a second multiplexer means operatively associated with said switching means to receive digital information from said multi-channel digital memory means and operative to receive analog information from a multi-channel function generator means.

18. The apparatus of claim 1 wherein said external component includes the coil of a current-to-force transducer.

* * * * *